Figure 1:
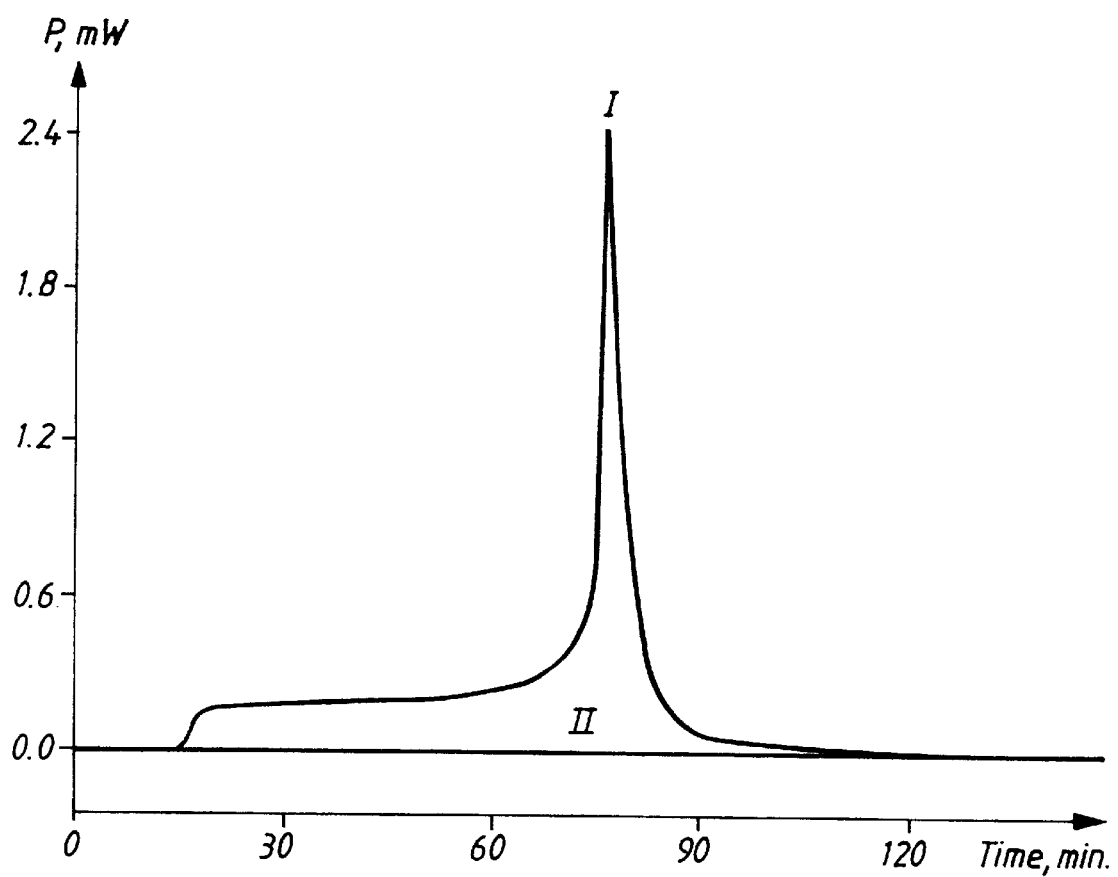

United States Patent [19]
Briggner et al.

[11] Patent Number: 5,874,063
[45] Date of Patent: *Feb. 23, 1999

[54] PHARMACEUTICAL FORMULATION

[75] Inventors: Lars-Erik Briggner, Höör; Katarina Bystrom, Genarp; Edib Jakupovic, Nykvarn; Eva Trofast; Jan Trofast, both of Lund, all of Sweden

[73] Assignee: Astra Aktiebolag, Sodertalje, Sweden

[*] Notice: The term of this patent shall not extend beyond the expiration date of Pat. No. 5,637,620.

[21] Appl. No.: 606,655

[22] Filed: Feb. 26, 1996

Related U.S. Application Data

[60] Continuation-in-part of Ser. No. 459,660, Jun. 2, 1995, Pat. No. 5,637,620, which is a division of Ser. No. 379,471, Jan. 30, 1995, abandoned, and a continuation-in-part of Ser. No. 479,494, Jun. 7, 1995, Pat. No. 5,562,923, which is a continuation of Ser. No. 129,204, Oct. 25, 1993, abandoned.

[30] Foreign Application Priority Data

Apr. 11, 1991 [SE] Sweden .................................. 9101090
Aug. 27, 1993 [SE] Sweden .................................. 9302777
Jan. 16, 1996 [SE] Sweden .................................. 9600141

[51] Int. Cl.$^6$ .............................. A61L 9/04; A61K 9/14
[52] U.S. Cl. .............................. 424/45; 424/46; 424/489
[58] Field of Search .................. 424/46, 45, 489

[56] References Cited

U.S. PATENT DOCUMENTS

| | | | |
|---|---|---|---|
| 3,987,192 | 10/1976 | Wright | 514/522 |
| 3,994,974 | 11/1976 | Murakami | 260/562 |
| 4,405,598 | 9/1983 | Brown | 424/45 |
| 4,476,130 | 10/1984 | Wade | 424/267 |
| 5,376,386 | 12/1994 | Ganderton | 424/499 |

FOREIGN PATENT DOCUMENTS

| | | |
|---|---|---|
| 0436110 | 7/1991 | European Pat. Off. . |
| 0508969 | 10/1992 | European Pat. Off. . |
| 8400294 | 2/1984 | WIPO . |
| 8607547 | 12/1986 | WIPO . |
| 9116882 | 11/1991 | WIPO . |

OTHER PUBLICATIONS

Orr et al. "The Mixing of Cohesive Powders," The Chem. Engin., pp. 12–19, Jan. 1973.
Carstensen et al. "Amorphous–to–crystalline Transformation of Sucrose," Pharm. Res. 7(12): 1278–1281, 1990.
Otsuka et al. "Effects of Surface Characteristics . . . ," J. Pharm. Pharmacol. 42: 606–610, 1990.
Ahlneck et al. "The Molecular Basis of Moisture Effects . . . ," Intl. J. Pharm. 62; 87–95, 1990.
Makower et al. "Equilibrium Moisture Content and Crystallization of Amorphous . . . ," Agric. Food Chem. 4(1): 72–77 1956.
Palmer et al. "X–Ray Diffractometer and Microscopic Investigation of Cystallization . . . ," Agric. Food Chem. 4(1): 77–81, 1956.
Ahlneck, C. "Chemical and Physical Stability of Drugs . . . ," E. Sandell Ed. pp. 80–92, 1993.
ElAmin et al. "Effects of Deactivation of Milled Materials on on the Tabletting . . . ," Swedish Annual Pharm. Congress, 1990.
Vidgren et al. "Physical Stability and Inhalation Behavior of Mechanically . . . ," Acta Pharm. Fennica, 98: 71–78, 1989.
Bates et al. "Deposition and Retention . . . ," Health Physics, Pergamon Press, 12: 173–207, 1966.
Faulds et al. "Formoterol: A Review of its Pharmacological Properties and Therapeutic . . . ," Drugs, 42(1): 115–137, 1991.

*Primary Examiner*—Theodore J. Criares
*Attorney, Agent, or Firm*—White & Case L.L.P.

[57] ABSTRACT

There are described finely divided particles of a pharmaceutical substance, wherein the substance when submitted to water vapor gives off heat of less than 1.2 Joules per gram, processes for their production and pharmaceutical formulations containing them.

20 Claims, 1 Drawing Sheet

PHARMACEUTICAL FORMULATION

This application is a continuation-in-part of application Ser. No. 08/459,660, filed Jun. 2, 1995 now U.S. Pat. No. 5,637,620, which is a divisional application of Ser. No. 08/379,471, filed Jan. 30, 1995, abandoned; and of Continuation In Part application Ser. No. 08/479,494, filed Jun. 7, 1995, now U.S. Pat. No. 5,562,923 which is a continuation of application Ser. No. 08/129,204, filed Oct. 25, 1993 (abandoned).

This invention relates to finely divided pharmaceutical materials, processes for their production and formulations containing them.

Finely divided particles either of drugs or of excipients are widely used in the pharmaceutical industry. Such particles are particularly of importance for drugs which are to be administered by inhalation where it is desired that the drug particles penetrate deep into the lung. Conventionally these finely divided drug particles are made by techniques such as micronization or grinding. A number of other techniques for their production are also available. Such techniques, and in particular micronization, can produce particles which have regions of partially amorphous structure, but which are generally sufficiently stable for pharmaceutical use. However, these particles are liable to change their structure when kept in an adverse environment, such as is usual when a drug is stored (e.g. in high humidity which can cause agglomeration), and/or is in use by a patient. The conventional techniques produce substances which when submitted to water vapor as set out below give off a considerable amount of heat.

We have now found that by treatment of fine particles, particularly of inhalation drugs and excipients therefor, their stability can be increased without substantially altering their particle size. The new particles according to the invention can also help to increase the respirable fraction of the powder when the drugs are used in dry powder inhalation devices. The new and more stable particles according to the invention have a greater degree of crystallinity than more conventional fine particles and are characterized in that they give off less heat than such conventional fine particles when submitted to water vapor as set out below.

According to the invention we provide finely divided particles of a pharmaceutical substance wherein the substance when submitted to water vapor gives off heat of less than 1.2 Joules per gram (J/g).

Preferably the substance gives off less than 1.0 J/g, more preferably less than 0.5 J/g, and most preferably less than 0.1 J/g.

The method of measuring the heat given off by the substance is set out below in Example A.

The inventive pharmaceutical substance consists of finely divided particles which may be of a drug, or of an excipient, or of a mixture thereof. Suitable drugs are those which are to be administered by inhalation, for example drugs for the treatment of asthma and other inflammatory diseases of the lung. Anti-asthmatic drugs include bronchodilators, anticholinergics, steroids, and prophylactic agents.

Bronchodilators which may be mentioned include terbutaline, e.g. as the sulfate, salbutamol, e.g. as the sulfate, fenoterol, e.g. as the hydrobromide, formoterol, e.g. as the fumarate dihydrate, salmeterol, e.g. as the xinafoate, clenbuterol, e.g. as the hydrochloride, procaterol, e.g. as the hydrochloride; bitolterol, e.g. as the mesylate; broxaterol and TA 2005 [8-hydroxy-5-(1-hydroxy-2-((2-(4-methoxyphenyl)-1-methylethyl)amino)ethyl)-2(1H)-quinolinone], e.g. as the monohydrochloride.

Steroids include budesonide; beclomethasone dipropionate; ciclesonide; fluticasone, e.g. as the propionate; mometasone, e.g. as the furoate and (22R)-6α,9α,-difluoro-11,β,21-dihydroxy-16α,17α-propylmethylenedioxy-4-pre.g.nen-3,20-dione (which has the generic name rofleponide).

Other inhalation drugs which may be mentioned include anti-cholinergic agents such as ipratropium bromide and oxytropium bromide, and prophylactic agents such as sodium cromoglycate and nedocromil sodium.

The substances of the invention may also include anti-histanmines, e.g. terfenadine.

Suitable excipients include those which are generally recognised as safe, for example for inhalation use, such as carbohydrates. Examples of suitable carbohydrates include sugars, e.g. lactose, glucose, fructose, galactose, trehalose, sucrose, maltose, xylitol, mannitol, myoinositol, raffinose, maltitol and melezitose. Other excipients which may be mentioned include amino acids, e.g. alanine and betaine, and compounds which enhance the absorption of drugs in the lung, for example surfactants, such as alkali metal salts of fatty acids, sodium tauro-dihydrofusidate, lecithins, sodium glycocholate, sodium taurocholate, and octylglucopyranoside. Still further excipients include antioxidants, e.g. ascorbic acid, and buffer salts.

Substances according to the invention can be in the form of solvates, e.g. hydrates; esters, or salts, or in the form of solvates or hydrates of such salts or esters.

The preferred drugs are terbutaline sulfate, salbutamol sulfate, ipratropium bromide, formoterol fumarate, salmeterol xinofate, budesonide and rofleponide, e.g. as their solvates, especially their hydrates, if such are formed.

The substances according to the invention may be in the form of mixtures of one or more components, e.g. a mixture of a drug with an excipient or a mixture of two or more drugs optionally together with an excipient. A specific mixture which may be mentioned comprises formoterol fumarate dihydrate, budesonide and lactose.

Preferred substance mixtures include the preferred drugs given above together with lactose or myoinositol.

The weight ratio between the drug(s) and excipient(s) is preferably in the range 1:1 to 1:1000, more preferably 1:1 to 1:500 and most preferably 1:1 to 1:200.

Particularly preferred are formulations containing from 4 to 40% w/w budesonide and from 96 to 60% w/w of lactose, or from 0.5 to 5% w/w of formoterol fumarate dihydrate and from 99.5 to 95% lactose. If more than one drug is used the weight ratio of the drugs and the unit dose should be such as to give the normal dosage of each drug.

The particle size of the finely divided particles, when it is desired that such particles should enter deep into the lung, e.g. when the substance is a drug, is preferably less than 10 microns and is preferably in the range 0.1 to 10 microns. When the finely divided substance is an excipient it may be of a particle size of less than 10 microns, e.g. of from 0.1 to 10 microns. It may however be desirable that the excipient does not enter the lung to any great extent and in that case the excipient may have a size of up to about 120 microns, e.g. of from about 30 to 120 microns. Particle sizes may be measured using for example a Malvern Master Sizer, a Coulter Counter or a microscope. In this specification when a particle size is specified it is a mass median diameter.

It is preferred that the substances of the invention have a surface area as measured by BET gas absorption, [e.g. as measured by a Flowsorb II 2300 or Gemini 2370, Micromeritics Co, USA, and described in ISO/TC24SC4N 55 (7th draft) and references therein] of from 3 to 12 $m^2/g$, and more preferably of from 3 to 9 $m^2/g$.

It is believed that the substances according to the invention have a crystalline form wherein there are relatively few, or substantially no, amorphous areas, e.g. as measured by X-ray powder diffraction. This is in contrast to conventional comminuted, e.g. micronized, substances.

The finely divided particles according to the invention may be used in a variety of pharmaceutical formulations, e.g. in producing tablets, or for filling into capsules for oral use. Preferred, however, are finely divided particles to be used to produce inhalation formulations. Thus they may be combined with pressurized gases, e.g. HFAs or CFCs with, or without, a surfactant to form pressurised metered dose aerosol formulations.

Alternatively, and more preferably, finely divided drug substances according to the invention may be used on their own or in admixture with excipients, e.g. lactose, which are of a larger, or of the same, particle size as the drug. Such powder formulations may be used in capsules, e.g. for use in the Spinhaler®, or in other inhalation devices, e.g. the Turbuhaler®, the Rotahaler®, the Diskhaler® or Diskus®. Drug substances according to the invention may also be treated further using known techniques, e.g. spheronization, to provide soft pellets, or soft granules, which are sufficiently strong to be filled into containers without disintegrating, but which are sufficiently weak to disintegrate into their fine constituent particles when administered by inhalation.

According to the invention we also provide a process for the production of substances according to the invention, which comprises treating a finely divided substance produced by a conventional method with a solvent in the vapor phase in a controlled manner such that the particle size of the substance does not change substantially, and then removing any excess solvent.

The solvent may be an organic solvent, e.g. an alcohol, ketone, ester or acetonitrile. Preferred is a lower alcohol, e.g. methanol, ethanol, n-propanol or isopropanol; a lower ketone, e.g. acetone or methyl ethyl ketone; or ethyl acetate. When an organic solvent is used it will tend to eliminate water from a substance which contains water in its crystal. In consequence we prefer not to use organic solvents to treat such substances. Alternatively, and preferably, the solvent is water, especially when the substance to be treated contains water in its crystal structure. A mixture of water and organic solvent may be used if desired.

The treatment of the substance with the solvent may be carried out under a variety of conditions which will vary with the substance to be treated, how that substance has been comminuted and with the solvent to be used. The variable parameters in the treatment will be inter alia the time, the temperature, the size of the batch to be treated, the container in which the treatment is to be carried out, the degree of mixing of the bulk substance and the means of introducing the solvent to the substance. It is of course desired that the aerodynamic properties of any substance which is to be administered by inhalation should not be adversely affected by the treatment.

When an organic solvent is to be used, the substance to be treated is preferably dried before it is subjected to the treatment. The drying may be carried out by conventional means, e.g. use of a vacuum or of an elevated temperature, or preferably by passing a dry gas through the substance. After the treatment any excess solvent may be removed by similar methods.

The process may be used to treat two or more different substances when in admixture, preferably in homogeneous admixture. When a mixture is to be treated and the particle size of both (or all) components is to be the same, the compounds may be mixed before comminution. Mixture before comminution tends to provide a homogenoeous mixture after comminution. The preferred method of comminution is micronization. Mixing may be carried out by conventional methods. When a mixture is to be treated the treatment may be carried out in one step when both substances are susceptible of the same treatment, or in two, or possibly more, steps when the substances require different treatments, e.g. different solvents, or different relative humidities/temperatures.

The treatment is carried out at a temperature/relative humidity (or the equivalent where an organic solvent is concerned) combination which suppresses the glass temperature of the substance(s) to be treated below the process temperature.

The treatment may be carried out at a temperature of from 0° to 100° C. and preferably 10° to 50° C. For practical reasons it is desirable to carry out the treatment at about ambient temperature.

The treatment is carried out at a relative humidity (or the equivalent where an organic solvent is used) such that the desired phase transition occurs. The optimal relative humidity will depend on the substance to be treated and can readily be determined by trial and error.

Depending on the temperature/relative humidity and glass temperature of the compound the relative humidity may be above 35%, above 50% or above 75%. Preferred is a relative humidity of from 35 to 85%.

The time necessary to effect the treatment will vary with batch size, relative humidity and a large number of other factors. The progress of the treatment with time can be monitored by taking samples and testing them in accordance with Example A and then the batch treatment time determined empirically for a given set of conditions.

The treatment may be carried out in any convenient closed container, e.g. a column or flask. The finely divided substance to be treated may be filled into the container and the solvent (or mixture of solvents) vapor, optionally in admixture with a gas, preferably an inert gas, e.g. nitrogen, may be passed through the bulk of finely divided substance. Care should be taken to ensure an even distribution of the solvent vapor through the bulk, e.g. by occasional and gentle stirring or by inverting the container from time to time. The solvent may be passed upwards through the bulk substance. The relative humidity (or equivalent when an organic solvent is used) may conveniently be adjusted by mixing a stream of dry gas with a stream of gas saturated with the treating solvent, the proportion of the two gas streams being varied to provide the required relative humidity (or its equivalent).

We have found that the treatment can readily be controlled to ensure that the particle size of the powders is substantially the same after the treatment as before.

The treatment process of the invention is generally inappropriate for the treatment of fine particles after they have been spheronized.

EXAMPLES

The invention is further illustrated but not limited by the following examples performed according to the following experimental procedure:

1. If necessary drying the substance(s) to be treated,

2. Mixing the substances in a defined ratio, if a mixture is desired,

3. Micronizing the substance, or mixture, to produce a particle size of less than about $10\mu$ as measured by a Coulter Counter.

4. Conditioning at a temperature/relative humidity (or the equivalent where an organic solvent is used) combination, which suppresses the glass temperature of the substance(s) involved below the process temperature. The glass temperature ($T_g$) is the temperature at which the mobility of an amorphous material undergoes changes from an immobile glassy state to a mobile rubbery state.

5. Drying with dry nitrogen or air, or in vacuum.

The percentages given are w/w.

Example 1

| Salbutamol sulfate (25%)/lactose (75%) | |
| --- | --- |
| Conditioned with water at relative humidity (RH) | 55–65% RH |
| Non-conditioned micronized substance mixture (J/g) | 5–8 |
| Conditioned micronized substance mixture (J/g) | <0.5 |

Example 2

| Ipratropium bromide (6%)/lactose (94%) | |
| --- | --- |
| Conditioned with water at relative humidity (RH) | 50–60% RH |
| Non-conditioned micronized substance mixture (J/g) | 6–8 |
| Conditioned micronized substance mixture (J/g) | <0.5 |

Example 3

| Formoterol fumarate dihydrate | |
| --- | --- |
| Conditioned with water at relative humidity (RH) | 75% RH |
| Non-conditioned micronized substance (J/g) | 6 |
| Conditioned micronized substance (J/g) | <0.5 |

Example 4

| Lactose (see FIG. 1) | |
| --- | --- |
| Conditioned with water at relative humidity (RH) | 50% RH |
| Non-conditioned micronized substance (J/g) | 10–14 |
| Conditioned micronized substance (J/g) | <0.5 |

Example 5

| Melezitose | |
| --- | --- |
| Conditioned with water at relative humidity (RH) | 50% RH |
| Non-conditioned micronized substance (J/g) | 12 |
| Conditioned micronized substance (J/g) | <0.5 |

Example 6

| Formoterol fumarate dihydrate (2%)/lactose (98%) | |
| --- | --- |
| Conditioned with water at relative humidity (RH) | 50% RH |
| Non-conditioned micronized substance mixture (J/g) | 10–14 |
| Conditioned micronized substance mixture (J/g) | <0.5 |

Example 7

3.6 Kg of micronized terbutaline sulfate was dried in a stainless steel column with 200 mm diameter at 90° C. in vacuum for 23 hours. The dried substance was cooled to about 30° C. and the pressure was normalized with ethanol-saturated nitrogen gas. 70 cc/min of ethanols-saturated nitrogen gas was then passed through the 200 mm diameter column for 60 hours to condition the substance. During this time the column was inverted a few times. The residual solvent was eliminated by purging with dry nitrogen gas for 2 hours and the conditioned product, about 3.5 kg, was packed in double plastic bags with a drying agent between the bags. The following results were determined according to Example A.

| Relative | Heat (J/g) | |
|---|---|---|
| humidity (%) | Non-conditioned substance | Conditioned substance |
| 58 | 3.6 | 0.1 |
| 75 | 6.2 | 0.1 |

Example 8

1 g Micronized salbutamol sulfate was kept at room temperature for 24 hours in a closed vessel containing a beaker filled with ethanol. The sample was removed and stored in a completely dry environment overnight in order to eliminate traces of ethanol. The following results were determined according to Example A.

| Relative | Heat (J/g) | |
|---|---|---|
| humidity (%) | Non-conditioned substance | Conditioned substance |
| 75 | 6–8 | 0.1 |

Example 9

1 g Spray-dried amorphous lactose was treated as in Example 8. The time it was kept in the saturated ethanol vapor was 100 hours. After removal of residual ethanol the sample was subjected to calorimetric analysis. The following results were determined according to Example A.

| Relative | Heat (J/g) | |
|---|---|---|
| humidity (%) | Non-conditioned substance | Conditioned substance |
| 75 | 40–44 J/g | <0.1 J/g |

Example 10

30 Kg of micronized lactose was placed in a stainless steel column which was surrounded by a heating mantle used to maintain the temperature of the column at 25° C. A flow of nitrogen gas was saturated with water vapor at 25° C. and then mixed with an equal volume of dry nitrogen to produce a gas stream of 50% relative humidity. This gas stream was passed into the base of the column at such a rate as to avoid fluidization of the lactose. The column was inverted from time to time to avoid the formation of channels in the lactose. When it was judged that the treatment was complete, a flow of dry nitrogen was introduced at the bottom of the column in order to remove any excess water.

The above procedure can be altered by varying the proportions of the wet and dry nitrogen streams to produce the desired relative humidity.

Example 11

| Budesonide (4.5%)/lactose (95.5%) | |
| --- | --- |
| Conditioned with water at relative humidity (RH) | 50–55% RH |
| Non-conditioned micronized substance mixture (J/g) | 11.3 |
| Conditioned substance mixture (J/g) | 0.9 |

Example 12

| Budesonide (36%)/lactose (64%) | |
| --- | --- |
| Conditioned with water at relative humidity (RH) | 50–55% RH |
| Non-conditioned micronized substance mixture (J/g) | 7.9 |
| Conditioned substance mixture (J/g) | 1.1 |

Example A

The heat (Joules per g or J/g) given off by the exemplified substances was measured as follows:

A small open plastic container holding a saturated NaCl solution (which produces a relative humidity of 75%) was placed inside a disposable glass ampoule which also contained a measured weight of the substance to be tested. The ampoule was then sealed and placed in a Thermal Activity Monitor 2277 calorimeter (Thermometrics AB, Sweden). The test procedure was carried out at an ambient temperature of 20°–23° C. and in a room having a relative humidity of 35–50%. A typical heat flow curve is shown in FIG. 1 in which the horizontal axis is time and the vertical axis is heat flow. Several batches of each substance or mixture were measured.

The relative humidity at which the procedure is carried out can be varied by changing the NaCl for other salts. Thus NaBr gives a relative humidity of 58%, and KCl of 84%. The choice of relative humidity should be such as to avoid complicating the measurement with extraneous transformations, e.g. change of polymorph.

Unless otherwise specified J/g was measured using a relative humidity of 75%.

Example B

Surface area of the micronized substance; and of the micronized substance both treated and untreated when it had been stored in a high humidity for 24 hours was measured. The measurements were carried out using a Flowsorb II 2300 as described above. The results are set forth below.

| Micronized substance ($m^2/g$) | Non-conditioned substance (after storage) ($m^2/g$) | Conditioned substance (after storage) ($m^2/g$) |
| --- | --- | --- |
| Terbutaline sulfate: | | |
| 11–12.5 | <3 | 7–9 |
| Salbutamol sulfate: | | |
| 8.4 | 3 | 5.9 |

The non-conditioned micronized substance has a great tendency to aggregate when stored as is shown by the low surface area when it has been stored at high humidity.

We claim:

1. Finely divided particles, with a mass median diameter of from 0.1 to 10 microns, of a pharmaceutical substance, which substance is selected from the group consisting of one or more inhalation drugs; an excipient suitable for inhalation; and a mixture of one or more inhalation drugs and an excipient suitable for inhalation, and wherein the substance when submitted to water vapor gives off heat of less than 1.2 J/g.

2. Particles according to claim 1, wherein the substance when submitted to water vapor gives off heat of less than 1.0 J/g.

3. Particles according to claim 2, wherein the substance when submitted to water vapor gives off heat of less than 0.5 J/g.

4. Particles according to claim 3, wherein the substance when submitted to water vapor gives off heat of less than 0.1 J/g.

5. Particles according to claim 1, wherein the substance is an inhalation drug.

6. Particles according to claim 5, wherein the substance is selected from the group consisting of a bronchodilator, an anticholinergic, a steroid and an antihistamine.

7. Particles according to claim 6, wherein the substance is selected from the group consisting of terbutaline sulfate, salbutamol sulfate, formoterol fumarate dihydrate, salmeterol xinofate, ipratropium bromide, budesonide and rofleponide.

8. Particles according to claim 1, wherein the substance is an excipient suitable for inhalation.

9. Particles according to claim 8, wherein the substance is lactose.

10. Particles according to claim 1 wherein the substance comprises a mixture of an inhalation drug and an excipient suitable for inhalation.

11. Particles according to claim 1, wherein the substance comprises lactose as the excipient in admixture with one or more inhalation drugs selected from the group consisting of terbutaline sulfate, ipratropium bromide, budesonide and formoterol fumarate dihydrate.

12. Particles according to claim 1 having a surface area as measured by BET gas absorption of from 3 to 12 $m^2/g$.

13. Particles according to claim 1 which have substantially no amorphous areas.

14. Finely divided particles, with a mass median diameter of from 0.1 to 10 microns, of a pharmaceutical substance, which substance comprises a mixture of lactose and terbutaline sulfate, and wherein the substance when submitted to water vapor gives off heat of less than 1.2 J/g.

15. Finely divided particles, with a mass median diameter of from 0.1 to 10 microns, of a pharmaceutical substance, which substance comprises a mixture of lactose and formoterol fumarate dihydrate, and wherein the substance when submitted to water vapor gives off heat of less than 1.2 J/q.

16. Finely divided particles, with a mass median diameter of from 0.1 to 10 microns, of a pharmaceutical substance, which substance comprises a mixture of lactose and budesonide, and wherein the substance when submitted to water vapor gives off heat of less than 1.2 J/g.

17. Finely divided particles, with a mass median diameter of from 0.1 to 10 microns, of a pharmaceutical substance, which substance comprises a mixture of lactose and ipratropium bromide, and wherein the substance when submitted to water vapor gives off heat of less than 1.2 J/g.

18. An inhalation formulation comprising an inhalation drug in the form of particles according to any one of claims 1 to 4.

19. A method of treatment of a patient suffering from an inflammatory disease of the lung which comprises administering an effective amount of particles according to claims 6 or 10 to the patient by inhalation.

20. Finely divided particles, with a mass median diameter of from 0.1 to 10 microns, of a pharmaceutical substance, which substance comprises a mixture of lactose, budesonide and formoterol fumarate dihydrate, and wherein the substance when submitted to water vapor gives off heat of less than 1.2 J/g.

* * * * *